(12) United States Patent
Smith et al.

(10) Patent No.: US 9,732,020 B2
(45) Date of Patent: Aug. 15, 2017

(54) PROCESS FOR THE ISOLATION OF 1,2,5,6-HEXANETETROL FROM SORBITOL HYDROGENOLYSIS REACTION MIXTURES USING SIMULATED MOVING BED CHROMATOGRAPHY

(71) Applicant: Archer Daniels Midland Company, Decatur, IL (US)

(72) Inventors: Brennan Smith, Decatur, IL (US); ChiCheng Ma, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/302,411

(22) PCT Filed: Apr. 10, 2015

(86) PCT No.: PCT/US2015/025271
§ 371 (c)(1),
(2) Date: Oct. 6, 2016

(87) PCT Pub. No.: WO2015/157617
PCT Pub. Date: Oct. 15, 2015

(65) Prior Publication Data
US 2017/0066702 A1    Mar. 9, 2017

Related U.S. Application Data

(63) Continuation of application No. PCT/US2014/033580, filed on Apr. 10, 2014, which is a continuation of application No. PCT/US2014/033581, filed on Apr. 10, 2014.

(51) Int. Cl.
| | |
|---|---|
| C07C 29/76 | (2006.01) |
| B01D 1/00 | (2006.01) |
| C07D 493/04 | (2006.01) |
| B01J 27/053 | (2006.01) |
| B01J 27/16 | (2006.01) |
| B01J 31/02 | (2006.01) |
| C07C 29/154 | (2006.01) |
| B01D 1/22 | (2006.01) |
| B01D 3/10 | (2006.01) |
| B01D 15/18 | (2006.01) |
| B01D 15/36 | (2006.01) |

(52) U.S. Cl.
CPC ............ *C07C 29/76* (2013.01); *B01D 1/22* (2013.01); *B01D 3/10* (2013.01); *B01D 15/1821* (2013.01); *B01D 15/361* (2013.01); *B01J 27/053* (2013.01); *B01J 27/16* (2013.01); *B01J 31/0225* (2013.01); *B01J 31/0227* (2013.01); *C07C 29/154* (2013.01); *C07D 493/04* (2013.01); *B01J 2231/4288* (2013.01); *B01J 2531/002* (2013.01); *B01J 2531/007* (2013.01)

(58) Field of Classification Search
CPC ........ C07C 29/76; B01D 1/22; B01D 15/1821
USPC ........................................................ 568/872
See application file for complete search history.

(56) References Cited

U.S. PATENT DOCUMENTS

| | | | | |
|---|---|---|---|---|
| 4,820,880 A | * | 4/1989 | Urbas | .............. C07C 29/60 568/861 |
| 5,107,018 A | * | 4/1992 | Schuster | .............. C07C 29/141 502/324 |
| 2009/0120878 A1 | * | 5/2009 | Hilaly | .............. C07C 29/76 210/656 |

* cited by examiner

*Primary Examiner* — Sikarl Witherspoon
(74) *Attorney, Agent, or Firm* — Vincent T. Kung

(57) ABSTRACT

A method of isolating and purifying 1,2,5,6 hexanetetrol (HTO) from a reaction mixture containing HTO and other byproducts of a hydrogenation reaction of a sugar alcohol and/or a mono- or di-dehydrative product of a sugar alcohol is described. The method involves contacting the mixture comprising HTO and other C1-C6 alcohols and polyols with a resin material adapted for chromatography under conditions where HTO preferentially associates with the resin relative to other components in the mixture, and eluting HTO from said resin with a solvent.

20 Claims, 6 Drawing Sheets

Conventional Synthesis and Separation Methods:

Present Purification Methods:

PROCESS FOR THE ISOLATION OF 1,2,5,6-HEXANETETROL FROM SORBITOL HYDROGENOLYSIS REACTION MIXTURES USING SIMULATED MOVING BED CHROMATOGRAPHY

PRIORITY CLAIM

The present application is a national phase application of International Application No. PCT/US2015/025271, filed Apr. 10, 2015, which claims benefit of priority of International Application Nos. PCT/US2014/033580 PCT/US2014/033581, both filed Apr. 10, 2014, the contents of each are incorporated herein by reference.

TECHNICAL FIELD OF INVENTION

The present invention relates to the synthesis and recovery of a hydrogenolysis product using chromatographic techniques. In particular, the invention pertains to the separation and purification of polyols derived from the hydrogenolysis of $C_6$ sugar alcohols.

BACKGROUND

In recent years, interest has grown in renewable source-based alternatives for organic functional materials that can serve as feedstocks for organic compound that have been made traditionally from petroleum or fossil-based hydrocarbons. As an abundant bio-based or renewable-resource, carbohydrates represent a viable alternative feedstock for producing such materials.

Biomass contains carbohydrates or sugars (i.e., hexoses and pentoses) that can be converted into value added products from renewable hydrocarbon sources. Sugar alcohols, such as sorbitol, mannitol, iditol, arbitol or xylitol, are one kind of sugar-derived compounds that can be further transformed into various kinds of materials, which in turn can be further modified.

The molecule 1,2,5,6-hexanetetrol ("HTO") is a by-product of the hydrogenolysis of sugar alcohols. Over the past century, various researchers have worked to prepare 1,2,5,6-HTO. For example, Zartman and Adkins reported in 1933 the synthesis of 1,2,5,6-hexanetetrol (1,2,5,6-HTO) by hydrogenolysis of sorbitol at 250° C. under 300 atm $H_2$ using copper-chromium oxide catalyst. (Zartman W., Adkins H., J. Am. Chem. Soc., 55, 4559 (1933).) In 1958, Gorin and Perlin reported the hydrogenolysis of 1,2-O-isoprpylidene-d-glucofuranose in a stirred batch under $H_2$ at 2000-2900 psi at 180° C. for 6 hrs in the presence of copper chromium oxide catalyst and the subsequent separation of 1,2,5,6-HTO by liquid-liquid extraction. (Gorin, P. A. J., Perlin, A. S., Canadian Journal of Chemistry (1958) v. 36, pp. 661-6.) In 1989, Urbas claimed the synthesis of "3,4-dideoxyhexitol" (1,2,5,6-hexanetetrol) via the catalytic hydrogenolysis of sorbitol, in a stirred batch reaction using 85% CuO and 15% Cr2O3 under 184-150 atm $H_2$ at 200° C. for 3 hrs and the subsequent acid catalyzed dehydration of 1,2,5,6-HTO to 2,5-bis(hydroxymethy)tetrahydrofuran (U.S. Pat. No. 4,820,880). Montassier describes a heterogeneous catalysis of sorbitol by a retro-Michael reaction to selectively yield glycerol from sorbitol favored on certain copper-based catalysts. (Montassier, C., et. al., Bulletin de la Societe Chimique de France (1989) (2), 148-55.) Ludwig mentions 1,2,5,6-HTO as a nearly 4% wt by-product in the synthesis of diols from sucrose, in a batch reaction, using CoO, CuO, Mn3O4, $H_3PO_4$, and $MoO_3$ at 160 C, under 280 bar $H_2$, for three hours but does not claim any methods for purification of the 1,2,5,6-HTO (DE 3928285 A1). Cargill mentions it as an impurity in a patent for the purification of sorbitol hydrogenolysis reactions using sweep gas (International Patent Application No. WO08057263). In 1997, Maier reported selective catalytic synthesis of 1,2,5,6-HTO by double asymmetric dihydroxylation of 1,5-hexadiene in one step, with purification of the meso compound by liquid-liquid extraction. (Maier, M. E., Reuter, S., Liebigs Annalen/Recueil (1997) (10), 2043-2046.) Also, by direct oxidation of unsaturated hydrocarbons, Milnas reports the synthesis of 1,2,5,6-HTO with $H_2O_2$ in anhydrous tert-butanol in the presence of $OsO_4$ (Milas, N. A., Sussman, S., J. Am. Chem. Soc., (1937) 59, 2345-7; U.S. Pat. No. 2,437,648).

1,2,5,6-HTO and other polyols having fewer oxygen atoms than carbon atoms may be considered a "reduced polyols." Corma et al. disclose generally that higher molecular weight polyols containing at least four carbon atoms can be used to manufacture polyesters, alkyd resins, and polyurethanes. (Corma et al., "Chemical Routes for the Transformation of Biomass into Chemicals," 107 Chem. Rev. 2443 (2007)). 1,2,5,6-HTO is mentioned, for example, as a starting material for the synthesis of diols (International Patent Application No. WO13163540) and for more esoteric multistep syntheses of small molecules (See, e.g., Machinaga, N., et al, Journal of Organic Chemistry, 1992, 57, 5178; Fitremann, J., et al, Tetrahedron, 1995, 51, 9581; Mayumi A., et al., Tetrahedron Letters (2000), 41(8), 1199-1203.).

As a useful intermediate in the formation of higher value chemicals, the industrial production of 1,2,5,6-HTO can be commercially important. For instance, 1,2,5,6-HTO is of primary commercial interest as a feedstock for the synthesis of adipic acid via continuous, selective oxidation. Adipic acid is used industrially to produce polyurethanes, plasticizers, lubricant components, polyester, and as food ingredient. Adipic acid's primary industrial outlet is in the production of Nylon-6,6 fibers and resins which, in 2010, accounted for 65% of the di-carboxylic acid's total 2.6 MM tons produced globally (See, e,g., Polen, T., et al., Journal of Biotechnology 167 (2013) 75-84).

Subsequent to the original work by Zartman et al. the literature is relatively sparse with references to 1,2,5,6-HTO compound, especially with regard to its production, isolation and purification. Given the recent increase in interest of using sugar-alcohols as a carbon resource and the value of 1,2,5,6-HTO as a potential commercial feedstock, various industrial and research entities are beginning to gather resources to develop better ways of making and separating this compound. Hence, a need exists for a method for isolating and purifying 1,2,5,6-HTO from a hydrogenolysis reaction mixture. In particular, a protocol that can be adapted to high-volume throughput systems would be welcome.

SUMMARY OF THE INVENTION

The present disclosure describes, in part, a method for the isolation and purification of 1,2,5,6-hexanetetrol (HTO) ($C_6H_{14}O_4$) from a reaction mixture derived from hydrogenolysis of sugar alcohols. The method involves: contacting a mixture comprising HTO and other $C_1$-$C_6$ alcohols and polyols with a resin adapted for chromatographic use, under conditions where HTO preferentially associates with the resin relative to other components in the mixture, and eluting HTO from the resin with a solvent. In particular, the resin employed is a non-functionalized material although other functionalized resin may also be used.

In another aspect of the invention, one can adapt the foregoing concept for high-throughput or continuous separations. One can implement a simulated-moving-bed (SMB) chromatographic system for the primary application.

Additional features and advantages of the present purification process will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section I—Terminology

Figure 1A:
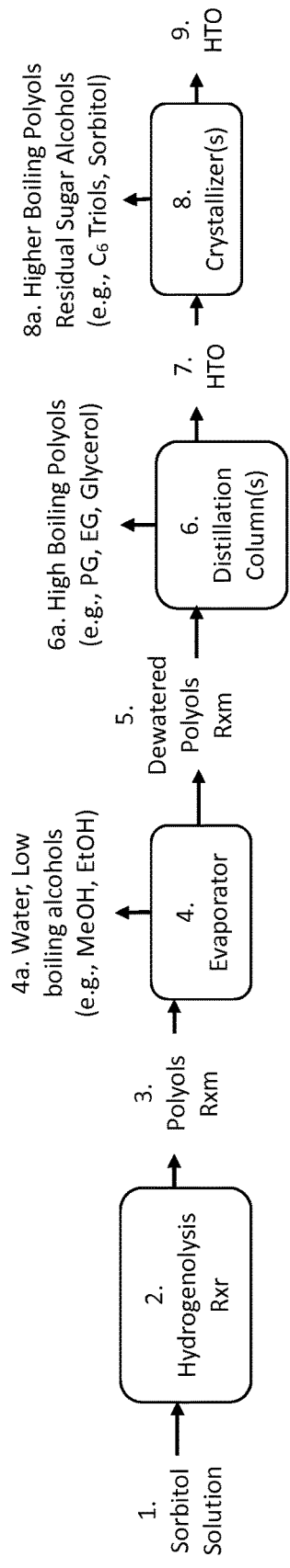
FIG. 1A is a flow chart representing conventional process for preparing and separating polyols from a hydrogenolysis reaction of sorbitol.

Before describing the present invention in detail, it is understood that the terminology used to describe particular embodiments is not intended to be limiting. As used in this specification and the appended claims, the singular forms "a," "an," and "the" include the plural referents unless the context clearly indicates otherwise. Unless defined otherwise in context, all technical and scientific terms used herein have their usual meaning, conventionally understood by persons skilled in the art to which the present invention pertains.

The term "bed volume" or "column volume" refers to the total volume of the packing material and interstitial liquid. The minimum volume of solvent necessary to wet the defined quantity of sorbent within the column can vary on the nature of the sorbent (e.g., ~120 µl per 100 mg of silica gel sorbent 60 Å, compared to ~600 µl per 500 mg of silica gel sorbent 60 Å).

The term "chromatographic resolution" refers to the degree of separation between consecutive analytes emerging from a chromatographic column.

The term "step-time" refers to the interval or dwelling time that a chromatographic columns in a simulated-moving bed chromatographic device remains at a particular position before the position rotates.

Section II—Description

The present invention describes, in part, a process for the separation and purification of chemicals derived from hydrogenolysis of sugar alcohols. Sorbitol hydrogenolysis is known to produce 1,2,5,6-hexanetetrol (HTO) and other polyols, although typically the reaction conditions are harsh and not economical. Various approaches can be used to make HTO. For instance, U.S. Pat. No. 4,820,880, discloses a method for producing HTO that involves heating a solution of a hexitol in an organic solvent with hydrogen at an elevated temperature and pressure in the presence of a copper chromite catalyst. Exemplary starting hexitols include sorbitol and mannitol. Water was found to adversely affect the reaction speed requiring the reaction to be performed in the absence of water and instead using ethylene glycol mono-methyl ether or ethylene glycol mono-ethyl ether as the sole solvent, which puts a solubility limit on the amount sorbitol that one can react. Under such conditions the maximum concentration of sorbitol that had been shown to be useful was 9.4% wt./wt. in ethylene glycol mono-methyl ether, which provided a molar yield of about 28% HTO. In a similar reaction where the sorbitol concentration was reduced to about 2% wt/wt in glycol methyl ether, the molar yield of HTO was 38% however the low concentration of reactants makes mono-such a process uneconomical. U.S. Pat. No. 6,841,085, discloses methods for the hydrogenolysis of 6-carbon sugar alcohols, including sorbitol, involving reacting the starting material with hydrogen at a temperature of at least 120° C. in the presence of a rhenium-containing multi-metallic solid catalyst. Nickel and ruthenium catalysts were disclosed as traditional catalysts for sorbitol hydrogenolysis, however these catalyst predominantly produced lower level polyols such as glycerol and propylene glycol and were not shown to detectably produce HTO or hexanetriols. (The contents of U.S. Pat. Nos. 4,820,880, and 6,841,085, are incorporated herein by reference.)

Other synthesis processes are described in International Application Nos. PCT/US2014/033580 and PCT/US2014/033581, the relevant contents of which are incorporated herein by reference. The processes described in these application involve contacting a solution comprising water and at least 20% wt./wt. of a starting compound selected from the group consisting of a $C_6$ sugar alcohol and a R-glycoside of a $C_6$ sugar, wherein R is a methyl or ethyl group, with hydrogen and a Raney copper catalyst for a time and at a temperature and pressure sufficient to produce a mixture containing one or more of the reduced sugar alcohols with a combined selectively yield of at least 50% mol/mol. In most advantageous embodiments of these methods the reaction solution comprises 20-30% wt./wt. water and 45-55% of a $C_2$-$C_3$ glycol. In an exemplary embodiment the solution comprises 20-30% wt./wt. water and 50-55% wt./wt. propylene glycol. These methods provide a combined selectivity yield for the reduced sugar alcohols of at least 70% mol/mol. A specific embodiment for making 1,2,5,6- hexanetetrol involved contacting a solution comprising 20-30% wt./wt. water, 45-55% of propylene glycol and at least 20% wt./wt. of a starting compound selected from the group consisting of $C_6$ sugar alcohol and a R-glycoside of a $C_6$ sugar, wherein R is a methyl or ethyl group, with hydrogen and a Raney copper catalyst for a time and at a temperature and pressure sufficient to produce a mixture containing the 1,2,5,6-hexanetetrol with a selectively yield of at least 35% wt./wt. In most advantageous embodiments the selectivity yield for 1,2,5,6-hexanetetrol is at least 40% wt./wt.

A.—Purification Process

Figure 1B:
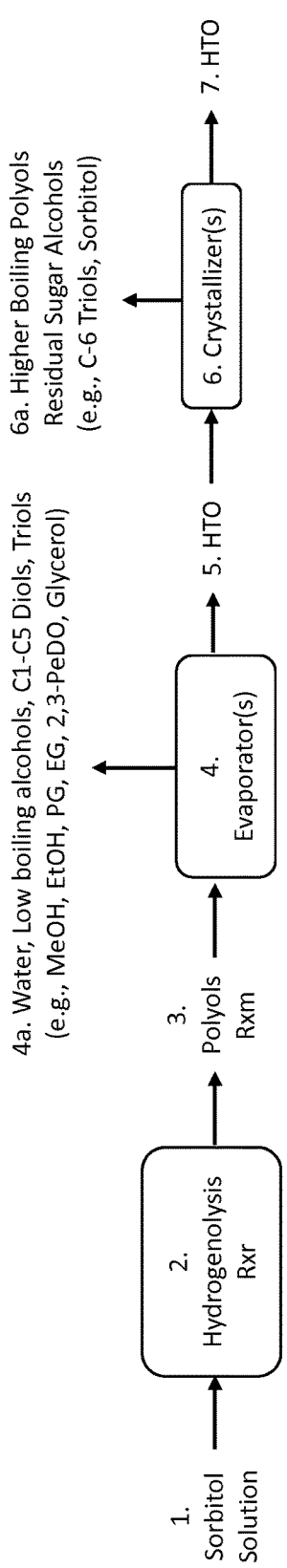
FIG. 1B is a flow chart showing an alternative conventional process for preparing and separating polyols from a hydrogenolysis reaction of sorbitol.
Figure 1C:
FIG. 1C is a flow chart illustrating another conventional process for preparing and separating polyols from a hydrogenolysis reaction of sorbitol.

Conventional processes for separating and purifying the desired HTO from other polyols and hydrogenolysis products have involved either complex techniques and/or multistep protocols. FIG. 1A is a flow chart that illustrates typical standard purification methods. The protocol involves first reacting sorbitol solution 1 in a hydrogenolysis reactor 2, transferring the hydrogenolysis-reaction, polyol-product mixture 3 to an evaporator 4 to drive off water and low-boiling alcohols 4a (e.g., methanol and ethanol), then subjecting the resulting dewatered polyol reaction mixture 5 to one or more distillations 6 and collecting the high-boiling polyols 6a (e.g., propylyene glycol (PG), ethylene glycol (EG), glycerol). Finally, the remaining crude bottoms products 7 are subjected to one or more rounds of crystallization 8 to remove any residual higher-boiling polyols and unreacted sugar alcohols 8a (e.g., $C_6$ triols, sorbitol), and produce a concentrated and purified HTO product 9. Alternatively, as depicted in FIG. 1B, the evaporator (or distillations) can be run at a higher temperatures and/or higher vacuum to remove glycerol before crystallization. FIG. 1C illustrates an alternative protocol that does not use an evaporator but involves solvent or liquid-liquid extraction (LLE) technique, in one or more solute contained in a feed solution is transferred to another immiscible liquid solvent.

Figure 2:
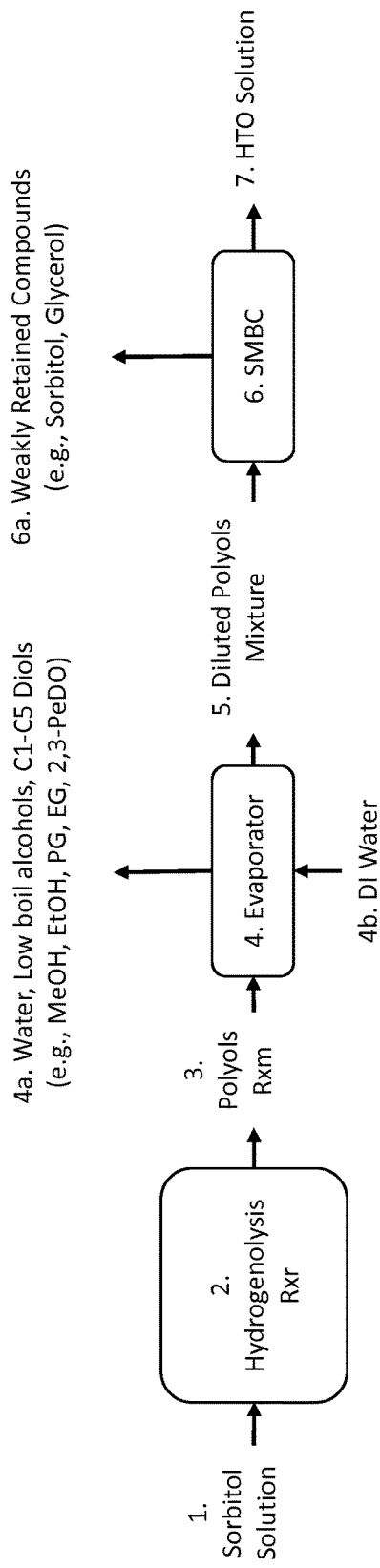
FIG. 2 is a flow chart showing a process for preparing and purifying 1,2,5,6-HTO from a hydrogenolysis reaction of sorbitol showing differences according to an embodiment of the present invention.

In comparison, the present purification process is simpler involving less steps or more cost efficient techniques. The present process employs a resin adapted for chromatographic purposes to separate and purify HTO from hydrogenolysis reaction mixtures. In certain embodiments the present method involves a combination of evaporation and simulated-moving bed chromatography. FIG. 2 presents a flow chart according to an embodiment of the present invention. After reacting sorbitol solution 1 in a hydrogenolysis reactor 2, transferring the hydrogenolysis-reaction, polyol-product mixture 3 to an evaporator 4 to drive off water, low-boiling alcohols, and $C_1$-$C_5$ diols 4a (e.g., MeOH, EtOH, PG, EG, 2,3-PeDO), de-ionized water (DI) 4b is added to dilute the polyol mixture 5, which is then subjected to chromatographic separation 6 using either non-functionalized or functionalized resins. Desirably the separation is performed with a non-functionalized resin in a simulated-moving bed (SMB) chromatographic device. The de-ionized water serves to dissolve the mixture and make the solution less viscous. In certain embodiments, it may be possible to use the water from the evaporator as the feed solvent for the SMB system, but probably not for the SMB eluent. Unlike the evaporators in the conventional processes, the evaporator in the present purification does not need to remove glycerol, only the lower boiling diols. This is because these lower boiling diols tend to retain on the SMB chromatographic resin, eluting along with the HTO, hence causing purity problems.

Isolation and purification of 1,2,5,6-hexanetetrol (HTO) by means of a combined process of evaporation and simulated-moving bed chromatography (SMBC) using an industrial grade resin has advantages over conventional processes. In part, the present invention contributes to a refinement of chromatographic separation techniques for difficult to purify organic species. These advantages include, for examples, cost savings and process efficiency associated with a continuous single-step separation method which more easily lends itself to high throughput automation, in contrast to the conventional need to employ multiple batch or semi-batch distillations. Another advantage is the ability to collect HTO product at a greater yield and purity. The inventive approach compares favorably to conventional approaches, in that it can be more efficient and cost effective than current processes.

According to a feature of the invention, we adapt liquid chromatography (LC) techniques to purify in a single operation a stream of 1,2,5,6-HTO from the large majority of other contaminants that are typically found in a hydrogenolysis reaction mixture. LC typically utilizes different types of stationary phases (i.e. sorbents) contained in columns, a pump that moves the mobile phase and sample components through the column, and a detector capable of providing characteristic retention times for the sample components and area counts reflecting the amount of each analyte passing through the detector. Analyte retention time varies depending on the strength of its interactions with the stationary phase, the composition and flow rate of mobile phase used, and on the column dimensions. Here, relatively large diameter columns and large particle sizes are employed to avoid pressure.

One may elute the chromatographic column with a variety of solvents, including for example, deionized (DI) water, methanol, butanol, isopropanol, simple $C_1$-$C_4$ aliphatic alcohols, or a mixture of these. Typically, the elution is with DI water alone. If a mixture of DI water and alcohol is used, the water and alcohol may be present respectively in a ratio in a range from about 50:1 to 1:50 (e.g., 40:1, 35:1, 25:1, 20:1, 12:1, 10:1, 5:1, or 1:30, 1:25, 1:20, 1:10, 1:8, etc.).

Lastly, one can perform another evaporation to remove excess water and eluent to collect the isolated 1,2,5,6-HTO as a solid if desired. The particular yields and purity of the separated 1,2,5,6-HTO can vary depending on the operational conditions. Nonetheless, according to embodiments of the present process, one can achieve about at least 40-45% wt./wt. yield, and about 70-75% purity. Typically, the yield is much higher, such as reported in Table 4, below. In general, examples of yield can range from about 50% or 55% wt./wt. to about 92% or 95% wt./wt., inclusive. More typically, the yield is in a range from about 60% or 65% wt./wt. to about 88% or 92% wt./wt. (e.g., 63%, 68%, 70%, 75%, 80%, 85%, 90% wt./wt.). Typically, the level of purity is about 80% or 85% to about 97% or 99.9%. More typically, the level of purity is about 86% or 87% to about 96% or 98%.

B.—Resin Materials

As stated previously, a variety of methods have been explored for the purification of 1,2,5,6-HTO including reactive extraction, distillation, and crystallization but each has met with problems. To overcome such problems, the present invention can employ either functionalized or non-functionalized resins. In certain embodiments, the non-functionalized resins appear to perform better. Non-functionalized resins do not bind the different species by means of an ionic charge; rather, non-functionalized resins work by a balance of hydrophilic and hydrophobic affinities. In the embodiments described, the adsorbent resins are unmodified and considered to be hydrophobic resins. Thus, hydrophobic organic species can bind to them and be retained in aqueous systems.

When a resin is not functionalized, the pH range of the input material can be in a range from about 0 to about 14. Typically, for non-functionalized resins the pH is about 5 to about 8, and desirably about 6.5 to about 7.5. When the resin is acid functionalized, an adjustment of the pH of the input material may be necessary for the polyol to have an affinity for the resin. Hence, the post-evaporative hydrogenolysis reaction mixture should be acidic, with a pH value of less than 7. For acid functionalized resin, the reaction mixture typically will have a pH of about 2.5 to about 5.8 or 6.5, more typically about 5.5-6.0. Similarly, an adjustment of the pH of the input material may be needed for base functionalized resins. In such situations, the post-evaporative reaction mixture will have a pH in a range of about 7 to about 14. Typically, this pH range is about 7 to about 9.5, and desirably about 7 to about 7.5.

In some embodiments, a type of resin employed in the separation of HTO can be classified as adsorbent poly (styrene-divinyl benzene) (PS-DVB) resins. The polystyrene is crosslinked with divinyl benzene. PS-DVB resins are an attractive adsorbent for extraction and separation of various types of compounds due to its stability over the pH range of 1-14. PS-DVB resins are known to have hydrophobic surfaces that highly retain non-polar compounds while poorly retaining polar compounds.

Hydrophobic-type PS-DVB resins are commercially available from a variety of vendors (e.g., Dow Chemical Company, Rohm & Haas Co., Mitsubishi Chemical Corporation, Purolite Corporation, Lanxess Corporation, etc.). Depending on the manufacturer and the particular specifications of each type of resin, the resin can have a variety of different pore sizes and surface areas, which can affect the physical and chemical nature of the resins, the quality of the separation and therefore the temperatures required for the different protocols. One can use a resin that has a surface area in the range between about 120 $m^2/g$ or 150 $m^2/g$ up to about 1100 $m^2/g$ or 1200 $m^2/g$. Typically, the surface area of the resin is in between about 150 $m^2/g$ or 200 $m^2/g$ to about 800 $m^2/g$ or 1000 $m^2/g$. In particularly adapted resins for certain organic solutions (e.g., corn syrup, fruit juices, HFCS, polyphenols, or natural extracts), the resin has a surface area of about 250 or 300 $m^2/g$ to about 600 or 750 $m^2/g$. The average pore diameter can range between about 50 Å or 100 Å to about 600 Å or 700 Å; typically between about 100 Å or 150 Å to about 450 Å or 500 Å. The mean diameter of the resin particles may range between about 300 μm or 350 μm to about 750 μm or 800 μm; typically, between about 400 μm or 500 μm to about 650 μm or 700 μm. The resins exhibit porosity in the range of about 0.90 or 0.95 ml/g to about 1.40 or 1.52 ml/g; typically about 0.97 ml/g to about 1.18 or 1.25 ml/g.

As the adsorbent resins exhibit non-polar or hydrophobic tendencies, this means that they preferentially adsorb the more hydrophobic organic compounds that are dissolved in water relative to polar compounds. For instance, a class of commercial ion-exchange resins from Rohm & Haas is AMBERLITE™ XAD™ polymeric adsorbents, which are very porous spherical polymers based on highly crosslinked, macroreticular polystyrene polymers. Their high internal surface areas can adsorb and then desorb a wide variety of different species depending on the environment in which they are used. For example, in polar solvents such as water, polymeric adsorbents exhibit non-polar or hydrophobic behavior and can adsorb organic species that are sparingly soluble. This hydrophobicity is most pronounced with the styrenic adsorbents. (In comparison non-polar solvents, such as hydrocarbons, etc. most adsorbents exhibit slightly polar or hydrophilic properties and so will adsorb species with some degree of polarity. This polarity is most pronounced with the acrylic adsorbents and the phenolic adsorbents.)

In the examples and embodiments described herein, four commercially available, industrial grade resins, are chosen based on their divergent physical characteristics, in order to screen adsorption properties for sorbitol and 1,2,5,6-HTO. Table 1, summarizes some of the physical and chemical attributes of the AMBERLITE™ brand, Optipore™ brand, and Dowex™ brand resins. These four resins respectively are representative of non-functional, strong base/anion, and strong acid/cation resins materials. Two non-functionalized resins, one mono-dispersed (XAD1600N) and one having Gaussian particle size distribution (V493) and two functionalized monodispersed resins, one strongly basic (1X8) and one strongly acidic (Dowex 99/310) are selected. Three of the resins, XAD1600N, Dowex 99/310, and Dowex 1X8 were designated chromatographic grade, the fourth (V493), was a highly cross-linked resin (temperature functional –15° C.-25° C.) used for adsorption of low level volatiles from industrial vapor streams. (Hence, not a conventional chromatographic resin material.) The mean diameter particle size of the resins can range from about 200 μm to about 850 μm. Typically, the particles are in a range from about 250 μm to about 500 μm, and desirably about 300 μm to about 450 μm.

TABLE 1

Characteristics of Resin Materials

| Resin | Functionality | Particle Size Distribution | Particle Size (μm) | Crosslink Density (%) | Exchange Capacity (eq./L) | Moisture Retention Capacity (%) | Surface Area ($m^2/g$) | Porosity (cc/g) | Density (lbs./cu.ft) |
|---|---|---|---|---|---|---|---|---|---|
| Amberlite XAD1600N | Non-functionalized | Monodispersed | 400 | ≤10 | n/a | 66-73 | ≥800 | ≥1.4 | 64 |
| Dowex 1X8 | Type I strong base anion | Monodispersed | 300 | 8 | 1.2 | 43-48 | — | — | 44 |
| Optipore V493 | Non-functionalized | Gaussian | 300-850 | ≥10 | n/a | 50-65 | >1100 | 1.16 | 21 |
| Dowex Monosphere 99/310 | Strong Acid | Monodispersed | 310 | 5 | >1.5 | 60-63 | — | — | 51 |

*All resins are polystyrene cross-linked with divinyl-benzene.

Other commercially available polystyrenic adsorbent resins, such as PuroSorb™ PAD adsorbents from Purolite, are made from clean monomers and have high surface areas that are free from any contaminants such as salts, metals and other minerals, making them especially suitable for food and pharmaceutical uses. However, such resins appear not to have been proposed or adapted for industrial separation of products from sugar-alcohol hydrogenolysis, in particular for HTO.

C.—Continuous Separation—Simulated Moving Bed Chromatography

We envision that the present separation process can be readily adapted for use in simulated-moving bed chromatographic systems. An embodiment that uses the present process makes feasible and commercially efficient the separation of 1,2,5,6-HTO from other polyols on non-functionalized resins using simulated-moving bed (SMB) chromatography. SMB chromatography utilizes a column bed containing the stationary phase resin segmented into a plurality of column segments, which are moved in a countercurrent direction relative to the input flow of the moving phase sample and eluent. The segments of the column in the SMB apparatus are typically mounted on a carousel beneath input ports for sample and eluent and output ports for raffinate and product. Once properly configured for a given separation, a SMB chromatographic separation can be run continuously with a constant flow of feed being input into one port, a constant flow eluent entering a second port, a constant flow of raffinate being withdrawn from a third port, and a constant flow of product being withdrawn from a fourth port. SMB chromatography can thus be optimized to purify a stream of 1,2,5,6-HTO in a continuous fashion. Pulse tests discussed in the following section provide a basis to evaluate different conditions and resins for application in SMB chromatography.

Figure 3:
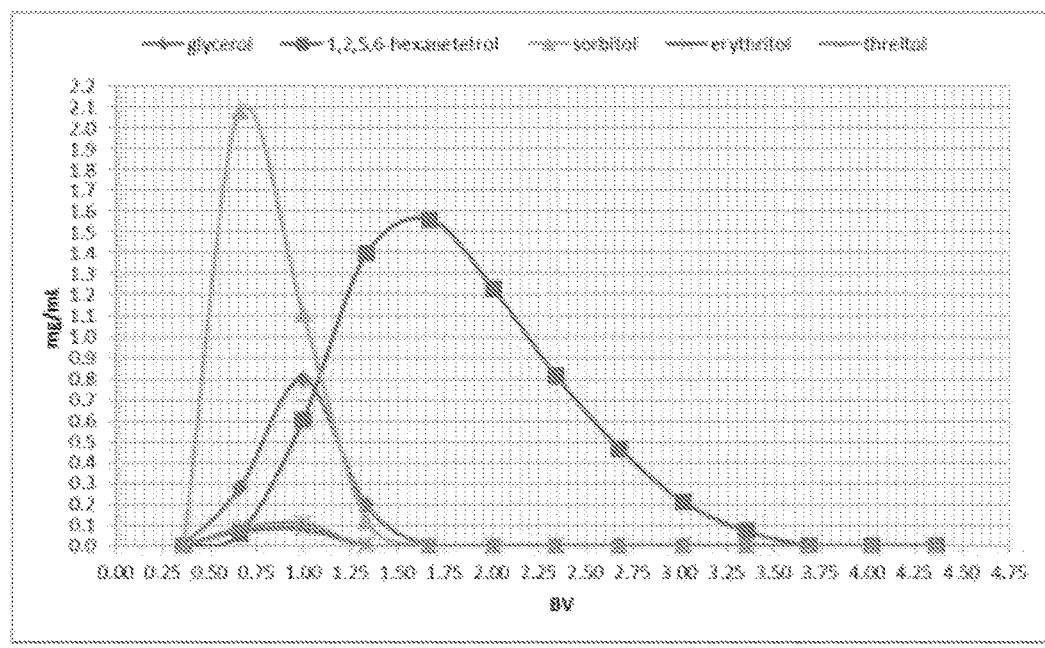
FIG. 3 is a graph showing pulse test results for the chromatographic separation of processed sorbitol hydrogenolysis reaction mixture.

FIG. 3 shows the results of a typical pulse test for the separation of 1,2,5,6-HTO and sorbitol, and the relative effectiveness of the present process to separate various different kinds of polyols or organic materials. For instance, the resolution for unreacted sorbitol, glycerol, erythitol, and threitol from 1,2,5,6 HTO in the hydrogenolysis reaction mixture can be achieved in a continuous chromatographic system. Persons of skill in the art understand that the separation performance of other particular resins may be either better or worse than that which is shown in the present illustrative results, and should be adjusted in each individual case may dictate.

Figure 4:
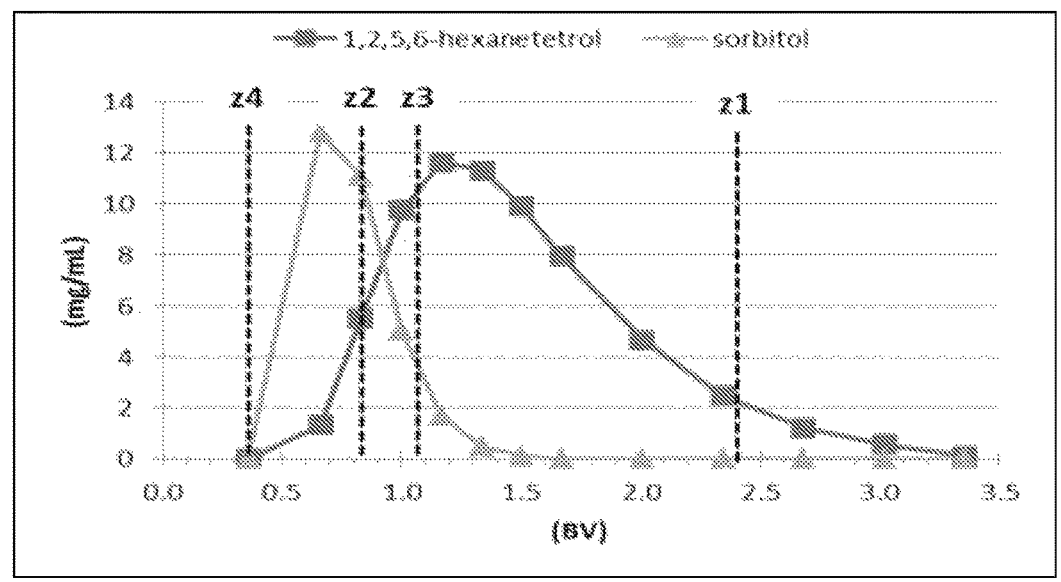
FIG. 4 is a graph showing pulse test results with zones dividing analytes.
Figure 5:
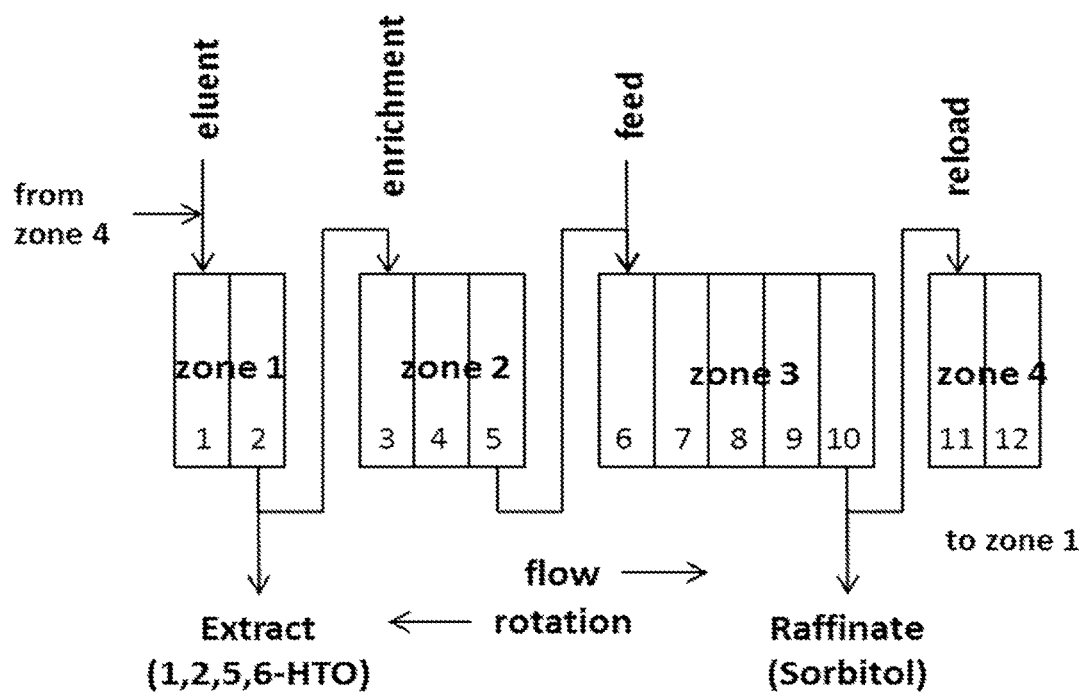
FIG. 5 is a diagram of a 500 cc simulated moving bed (SMB) system configured according to an embodiment of the present invention.

In FIG. 4, a pulse test result is divided into zones in order to translate the pulse test separation to a continuous simulated moving bed system (SMB). Theoretical zone flow rates for adaptation to a SMB separation method are determined from the pulse test, as detailed in Table 2. Table 3 shows the actual flow rates for zones adapted to a 12 column, combined 500 cc, carousel-type, SMB chromatography system, loaded with a Gaussian non-functionalized resin (V493), configured according to the diagram in FIG. 5. According to this embodiment, the sorbitol hydrogenolysis reaction mixture thin-film evaporative (TFE) distillate bottoms, processed according to the method detailed above, were diluted to approximately 30% wt. in deionized water and fed into the SMB system depicted in FIG. 5, which was run continuously at room temperature (~18-22° C.), with a fifteen minute step time, for 9.25 hours, or three full rotations. The raffinate and extract were collected, sampled and analyzed according to the method detailed above. The yield and purity of 1,2,5,6-HTO and sorbitol recovered according to the present process were calculated and summarized in Table 6.

The yield of HTO and sorbitol achieved respectively is 88.0% and 99.6%. The purity of each compound respectively is 99.6% and 88.8%.

TABLE 2

Zone flows translated from pulse test results

| Zone | Zone flows (mL/min) |
|---|---|
| 1 | 7.00 |
| 2 | 2.50 |
| 3 | 3.25 |
| 4 | 1.00 |

TABLE 3

Pump flows for SMB translated from zone flows from pulse test

| Pump | pump flows (mL/min) | pressure (psi) | Configuration |
|---|---|---|---|
| Eluent | 6.00 | 9-11 | 2 |
| Enrich | 2.50 | 13 | 3 |
| Feed | 0.75 | 11.00 | 5 |
| Reload | 1.00 | 8 | 2 |

TABLE 4

Yield and purity from the continuous SMB chromatography experiment

| | 1,2,5,6-HTO | Sorbitol (unreacted) |
|---|---|---|
| Yield: | 88.0% | 99.6% |
| Purity: | 99.6% | 88.8% |

Depending on the chemical and physical characteristics of the resin materials employed in the chromatographic separation, the resin materials may be subject to an operational temperature that ranges from about 10° C. or 15° C. to about 95° C. or 100° C., so long as the mechanism of chromatography is not adversely interfered with to impede flow. Typically, the temperature is at about ambient room temperature or in a range from about 18° C. or 20° C. to about 75° C. or 90° C. (e.g., 22° C., 27° C., 30° C., 35° C., 40° C., 45° C., 50° C., 55° C., 60° C., 65° C., 70° C., 78° C., 80° C., 85° C.). The temperature range can be from about 15° C. or 20° C. to about 88° C. or 100° C. for the non-functionalized resins. The temperature range can be from about 17° C. or 20° C. to about 50° C. or 60° C. for the functionalized resins.

Table 5 presents operational ranges flow rates as prescribed according to certain embodiments, but which may vary and can influence the operational parameters of the SMB chromatography.

TABLE 5

Flow rate as written:

| Zone (#) | Flow rate (mL/min.) | ST (min.) | Col. vol. (mL) | BV (mL/mL) |
|---|---|---|---|---|
| 1 | 6.88 | 15 | 43 | 2.40 |
| Raff. | 4.39 | 15 | 43 | |
| 2 | 2.49 | 15 | 43 | 0.87 |
| 3 | 3.24 | 15 | 43 | 1.13 |
| Prod. | 2.24 | 15 | 43 | |
| 4 | 1.00 | 15 | 43 | 0.35 |

Expressed generally, Table 6 shows the flow rate for an amount of material that can be processed when constant bed volume (BV) and column volume is used, and step-time (ST) is variable. When the time interval that each column dwells between changing position in the SMBC changes from about 5 minutes to 15 minutes to 30 minutes, the flow rate for each zone of the SMBC decreases proportionately for each step time.

TABLE 6

Flow Rate for each Zone of SMB (ST)

| Flow (mL/Min.) | | 1 | Raff. | 2 | 3 | Prod. | 4 |
|---|---|---|---|---|---|---|---|
| ST (min.) | 5 min. | 20.6 | 13.2 | 7.5 | 9.7 | 6.7 | 3.0 |
| | 15 min. | 6.9 | 4.4 | 2.5 | 3.2 | 2.2 | 1.0 |
| | 30 min. | 3.4 | 2.2 | 1.2 | 1.6 | 1.1 | 0.5 |

Alternatively, the flow can be expressed in terms of bed volumes (BV) for use in potential industrial scale operations. Table 7 shows the parameters for flow rate range when the step time (ST) and column volume are constant and BV is variable—Low (0 to 3 BV), Medium (>3 to 8 BV), and High (>8 to ≥10 BV).

TABLE 7

Flow Rate for each Zone of SMB (BV)

| Flow | | 1 | Raff. | 2 | 3 | Prod. | 4 |
|---|---|---|---|---|---|---|---|
| BV | Low | 4.6 | 2.4 | 2.2 | 2.6 | 2.0 | 0.6 |
| | Med. | 6.9 | 4.4 | 2.5 | 3.2 | 2.2 | 1.0 |
| | High | 8.6 | 5.7 | 2.9 | 3.7 | 2.0 | 1.7 |

As the data from FIGS. 3 and 4 suggest, successful separation of 1,2,5,6-HTO from the other polyols and unreacted materials in the hydrogenolysis product feed tends to occur within a range of about 1 bed volume to about 3 bed volumes. Nonetheless, this does not necessarily limit the process as various factors, such as flow rate, feed concentration or loading can affect the purity of the target compound eluent.

In operation, certain selectivity capacity parameters should be maintained. For instance in the pulse test targets, the peaks should overlap significantly while maintaining good purities within the leading-edge and trailing edge regions. This facilitates maximum productivity potential. For most economical SMB operation, it is desirable that the target compound (all peaks) should elute within about 1 to 3 BV. (See, Pynnonen, B., et al, Evaluate SMB Chromatography for Your Separation. *Chemical Processing* [Online] 2010 http://www.chemicalprocessing.com/articles/2010/079.html.) Selectivity should be greater than (>) 2 for reasonable productivity. (See, Cox, Geoffrey B., *Simulated Moving Bed Chromatography and Chiral Compounds*, ISPE, Toronto, Sep. 29, 2005.)

Section III—Empirical

The present invention is further demonstrated by the following example.

A.—Feedstock Generation

Experiments with heterogeneous metal catalysts in continuous flow, trickle bed reactors, at the 30 cc and pilot scales, have shown efficacy for the synthesis of 1,2,5,6-HTO from sorbitol. D-sorbitol 35% in deionized water with 0.5-1.0% wt sodium hydroxide co-catalyst was fed into a 14 L trickle bed reactor. The reactor was packed with 14 L, 5% wt nickel 1% wt rhenium on carbon and used, along with flow rate, to calculate liquid hourly space velocity (LHSV, $hr^{-1}$) of the feed. Sorbitol solution was fed into the 165° C.-200° C. reactor at 0.5-1.0 $hr^{-1}$, under 1800 psi $H_2$ flowing at 20 SCFM. The reactor product was sampled and prepared by derivatizing with pyridine and acetic anhydride at 70° C. and analyzed using a J&W DB-5 MS UI column (30m×0.25 mm×0.25 um) on an Agilent 7890 equipped with an FID detector. Samples were analyzed for water using a Mettler Toledo volumetric Karl Fischer auto-titrator. Carboxylate analysis was performed with a Showdex SH-1011 strong acid ion exchange analytical column (300×7.8mm) on an Agilent 1260 HPLC equipped with a diode array detector at 210 nm.

According to an embodiment, the method of purifying 1,2,5,6 hexanetetrol from a reaction mixture containing HTO and other byproducts of a hydrogenation reaction of a sugar alcohol and/or a mono- or di-dehydrative product of a sugar alcohol, involves:

a. contacting the reaction mixture with a strong acid ion exchange resin to obtain a first eluent fraction depleted of cationic species;

b. contacting the first eluent fraction with a strong basic ion exchange resin to obtain a second eluent fraction depleted of anionic species;

c. evaporating the second eluent fraction under vacuum and retaining a first bottoms fraction depleted of water, volatile alcohols and lower boiling diols;

d. subjecting the first bottoms fraction to a thin film evaporation and retaining a second bottoms fraction depleted of glycerol;

e. contacting the second bottoms fraction with a non-functionalized chromatography resin, wherein the resin is loaded into a simulated moving bed chromatography apparatus;

f. eluting the chromatography resin with deionized water; and g. collecting a fraction enriched in HTO as compared to said hydrogenation reaction mixture.

Derived from $C_6$ sugars, the sugar alcohol can be for example: sorbitol, mannitol, galactitol, fucitol, iditol, inositol, maltitol, and mixtures thereof.

In the present example, the hydrogenolysis product mixture was contacted with an ion exchange (IX) resin before contacting the effluent with a resin material adapted for chromatography because the sorbitol hydrogenolysis reaction employed sodium hydroxide as a homogeneous co-catalyst along with the heterogeneous NiRe on carbon catalyst. The IX resin is used to purify the reaction mixture by removing ionic organic and inorganic species before the mixture is fed into the chromatographic separation columns. In embodiments with other sorbitol hydrogenolysis reactions that do not use as a reagent or produce as a by-product significant ionic organic or inorganic species (e.g.: Raney copper, CuRe on Zr, or Cu on carbon heterogeneous catalysts), the IX step prior to chromatographic separation would likely be unnecessary.

When an IX column is needed the ion exchange reaction can be either 1) a single-step mixed-bed reaction, or 2) a two-step acid-first, base-second reaction or the reverse base-first, acid-second reaction. The fraction of the ion exchange reactions can be concentrated by evaporation. The evaporation method can be selected from the group consisting of vacuum evaporation, thin film evaporation (TFE), and a combination of both vacuum and TFE. In certain embodiments, vacuum evaporation can be performed at a temperature between about 110° C. to about 160° C., and under a pressure in a range from about 100 Torr to about 10 Torr. TFE can be performed at a temperature in a range from about 150° C. to about 175° C. or 180° C., under a pressure from about 10 Torr to less than 1 Torr (e.g., 0.1 Torr).

Table A summarizes the analyte distribution from the hydrogenolysis reaction. The reaction mixture was then passed over strong acid (Dowex 88) and strong base (Dowex 22) ion exchange resins to remove sodium and carboxylates respectively. The ion exchanged reaction mixture was heated, under vacuum, to remove water, volatile alcohols (methanol, ethanol, propanol) and finally propylene and ethylene glycols. The bottoms from the evaporation, comprised primarily of sorbitol, glycerol, $C_4/C_5$-sugar alcohols, 1,2,5,6-HTO other triols and trace diols, was then fed into a 2-inch Pope thin film evaporator (TFE) in the molecular still (internal condenser) configuration to remove glycerol. The hydrogenolysis reaction mixture was preheated to 75° C. and fed at a rate of 3.87 g/min, into the Pope still. The TFE skin temp was set at 160° C., the bottoms temp was 95° C., the blade speed was 505 rpm, the internal condenser was kept at 63° C., and the vacuum was held at 9.7 Torr. The final distillate fractions were pooled and bottoms and distillate analyzed. The bottoms fraction from the TFE, was used for resin experiments detailed below.

TABLE A

Analyte Distribution of Streams from Sorbitol Hydrogenolysis Separation

| Analytes | Hydrogenolysis Reaction Mixture | PG Dist Bottoms | TFE Dist Bottoms |
|---|---|---|---|
| Propylene glycol (%) | 14.043 | 0.097 | 0.000 |
| Ethylene glycol (%) | 5.473 | 5.561 | 0.184 |
| 1,2,5,6-Hexanetetrol (%) | 2.103 | 38.313 | 52.570 |
| Carboxylic Acids (%) | 1.679 | 0.000 | 0.000 |
| 1,2-Butanediol (%) | 1.629 | 0.079 | 0.044 |
| Sorbitol (%) | 1.485 | 20.691 | 26.810 |
| 2,3-Butanediol (%) | 1.236 | 0.000 | 0.000 |
| Glycerol (%) | 0.783 | 14.370 | 9.410 |
| Other Triols (%) | 0.692 | 14.486 | 8.617 |
| Di-PG (%) | 0.300 | 6.295 | 0.000 |
| C-4 Sugar Alcohols (%) | 0.070 | 2.312 | 5.257 |
| Other Diols (%) | 0.060 | 0.563 | 0.000 |
| C-5 Sugar Alcohols (%) | 0.028 | 0.525 | 0.546 |
| Na (ppm) | 6140 | 0.000 | 0.000 |
| Water (%) | 67.21 | 0.000 | 0.000 |

Carboxylic Acids include: Glyceric, Glycolic, Lactic, Formic, Acetic, Levulinic, Propionic; C4-Sugar Alcohols include: Erythritol, Threitol; C5-Sugar Alcohols include: Xylitol, Arabitol; Other Diols Iiclude: 1,2-Pentatediol, 2,3-Pentanediol, 1,2-Hexanediol; Other Triols include: 1,2,3-Butanetriol, 1,2,4-Butanetriol, 1,2,5-Pentanetriol, 1,2,6-Hexanetriol, 1,4,5-Hexanetriol, 1,2,5-Hexanetriol.

B.—Resin Screening—Beaker Tests

Four commercially available resins are used. They were filtered from their bulk water using a Buchner funnel, dried under vacuum at room temperature in a Rotovap and weighed into beakers using an analytical balance. The thin-film evaporative (TFE) bottoms stream from Table A was diluted with deionized water and weighed into the beakers containing the resins using an analytical balance. Each of the four resins, was tested at increasing concentrations, to gauge adsorptive capacity. The beakers containing resin and hydrogenolysis TFE distillate bottoms were placed on a shaker, at room temperature and mixed overnight. The supernatant was measured according to the methods described above.

Figure 6:
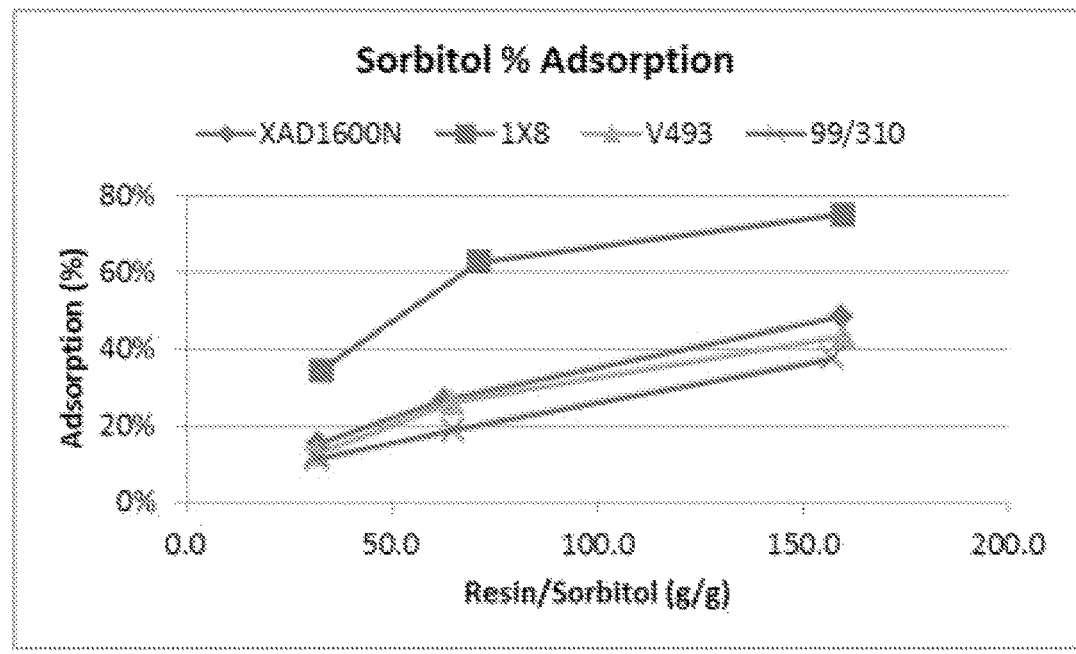
FIG. 6 is a graph showing the percent adsorption vs resin loading for sorbitol from thin-film evaporative (TFE) distillate bottoms.
Figure 7:
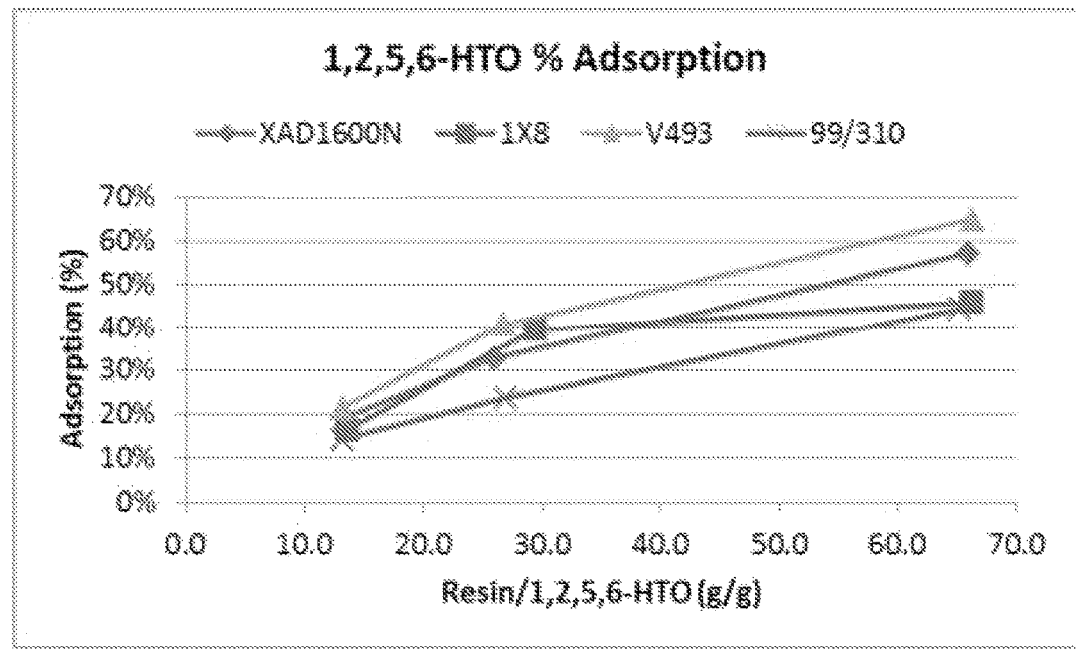
FIG. 7 is a graph showing the percent adsorption vs resin loading for 1,2,5,6-HTO from thin-film evaporative (TFE) distillate bottoms.

According to an embodiment of the present invention, FIGS. 6 and 7 show the percent (%) adsorption for each of the four resins described in the foregoing, at increasing loading, for sorbitol and 1,2,5,6-HTO respectively. The figures contrast adsorbency and capacity of the resins.

In FIG. 6, the Type I strong base anion resin (Dowex 1X8) demonstrated the best performance of the four kinds of sample resin materials for adsorbing sorbitol at about 32-78% per resin/sorbitol (g/g). This amount of sorbitol adsorbed is about 10% to about 20-28% greater than the next best performing resin material (AMBERLITE™ XAD1600N), which is a non-functionalized resin and it adsorbed about at about 17%-50%. The two other remaining resins—non-functionalized (Optipore V493) and strong acid-functionalized (Dowex Monosphere 99/310)—performed comparable to the XAD1600N material.

In FIG. 7, of the four resin materials tested, the material that performed the best for adsorbing 1,2,5,6-HTO appears to be a Gaussian non-functionalized resin (Optipore V493), which adsorbed about 20% to about 65% of the HTO per amount resin/HTO (g/g). This non-functionalized resin adsorbed about 5-7% more than the next best performing material which is a mono-dispersed non-functionalized resin material (AMBERLITE XAD1600N). The performance of the two remaining acid and base functionalized resins were comparable but at a little less (e.g., difference of ~5-10%) absorbency than that of the non-functionalized resins.

Table B summarizes the data for each of the beaker tests. The results of these beaker tests suggested, surprisingly, that the Gaussian non-functionalized resin (V493) had the best selectivity for 1,2,5,6-HTO and was selected for use in subsequent pulse tests.

TABLE B

Data from Beaker Tests

| Resin | Type | Resin* (g) | Resin/ 1,2,5,6- HTO (g/g) | 1,2,5,6- HTO Adsorption (%) | Resin/ Sorbitol (g/g) | Sorbitol Adsorption (%) |
|---|---|---|---|---|---|---|
| XAD1600N | Adsorb Mono-dispersed | 25.44 | 65.95 | 57% | 159.52 | 49% |
|  |  | 10.01 | 25.96 | 33% | 62.79 | 27% |
|  |  | 5.13 | 13.29 | 19% | 32.15 | 15% |
| 1X8 | Strong Base | 25.50 | 66.11 | 46% | 159.91 | 75% |
|  |  | 11.35 | 29.44 | 39% | 71.20 | 63% |
|  |  | 5.24 | 13.59 | 16% | 32.87 | 35% |
| V493 | Adsorb Gaussian | 25.55 | 66.24 | 65% | 160.21 | 43% |
|  |  | 10.28 | 26.65 | 41% | 64.47 | 26% |
|  |  | 5.08 | 13.16 | 21% | 31.83 | 13% |
| 99/310 | Strong Acid | 25.12 | 65.13 | 44% | 157.54 | 38% |
|  |  | 10.37 | 26.88 | 24% | 65.02 | 19% |
|  |  | 5.08 | 13.17 | 14% | 31.86 | 11% |

C.—Resin Screening—Pulse Tests

A slurry of non-functionalized adsorptive resin (V493), in deionized water was added to a #11 Ace Glass jacketed chromatography column (1.10 cm ID×45 cm L) to the 43 cc mark. A solution of sorbitol hydrogenolysis reaction mixture thin-film evaporative (TFE) distillate bottoms, processed as described above, was weighed, using an analytical balance and added onto the top of the resin using a polyethylene pipette. The column was capped with Teflon adapters and connected using 0.0625" Teflon tubing and Swagelok fittings to a peristaltic pump at the influent and an automatic fraction collector at the effluent. Deionized water was pumped through the column at room temperature using a peristaltic pump set to a flow rate of 1.45 mL/min. The effluent from the column was collected using an automatic fraction collector set to collect a fraction every 60 seconds. A total of 120 fractions were collected and every fifth fraction, starting at fraction one, was analyzed according to the procedure detailed above.

Figure 8:
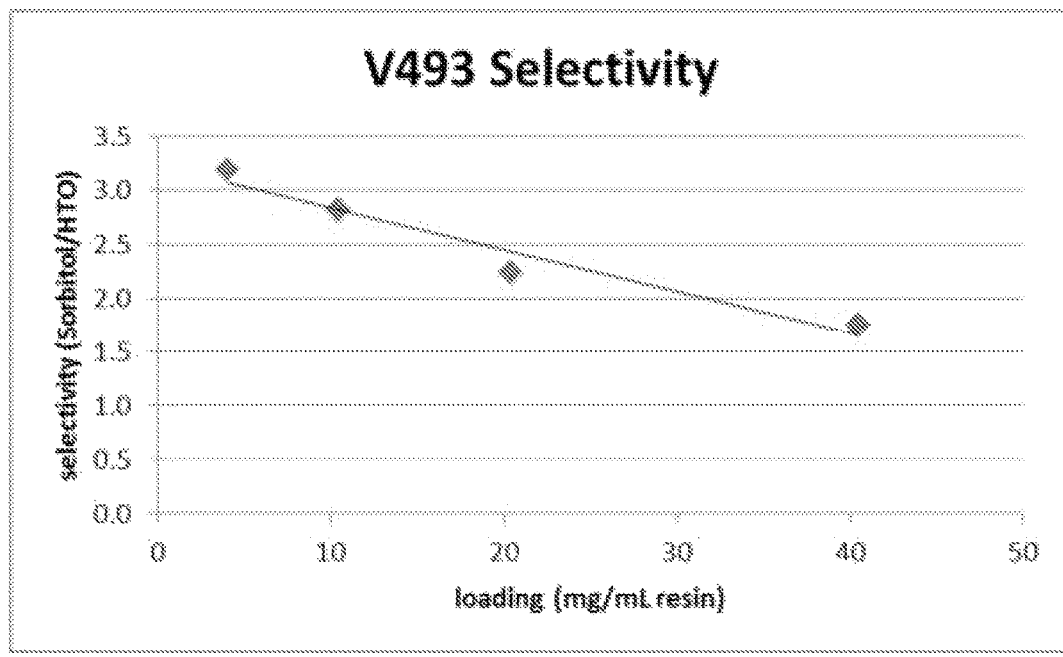
FIG. 8 is a graph showing the relative selectivity of a chromatographic resin (e.g., V493) according to an embodiment of the present invention for 1,2,5,6-HTO from sorbitol.
Figure 9:
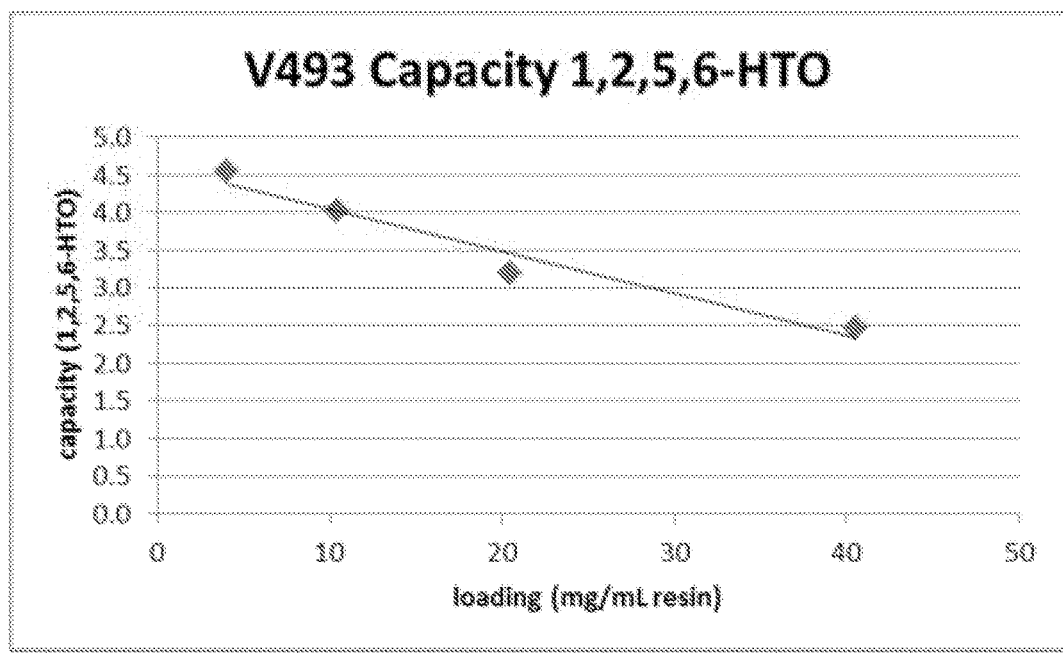
FIG. 9 is a graph showing the capacity of a non-functionalized resin (V493) according to an embodiment of the present invention for 1,2,5,6-HTO separation.

FIGS. 8 and 9 respectively present the results in selectivity and capacity, relative to column loading for the separation of 1,2,5,6-HTO from sorbitol using a Gaussian particle distribution, non-functionalized resin material (V493). The equation for concentration is: mg analyte/mL Resin =Wt.% Analyte*g Mixture/mL Resin (in column) At four different concentrations (5, 10, 20, and 40 mg/mL resin) the selectivity of the resin appears to be about 3.2, 2.8, 2.3, and 1.7 sorbitol/HTO, respectively. At the same concentrations, the resin capacity for HTO appears to be about 4.6, 4.0, 3.2, and 2.5, respectively. The data in FIGS. 8 and 9, suggests that as the loading of the feed of hydrogenolysis product mixture increases the selectivity of the resin between sorbitol and HTO and the resin capacity for HTO decreases respectively. Hence, one should balance the volume or concentration of the feed loading and the selectivity of the separation as represented in the pulse test of FIGS. 3 and 4, which shows the results of a typical pulse test for the separation of 1,2,5,6-HTO and sorbitol, and indicates the relative efficacy of the separation of HTO from other polyols and unreacted sorbitol.

The calculations of capacity and selectivity can be expressed respectively according to the following equations:

Capacity Factor—k
(also known as Retention Factor and Relative Retention)

$$k=(tR-tO)/tO$$

wherein,
tR=Retention Time of Peak,
tO=Retention Time of the Unretained Peak
Selectivity—a
Separation Factor (Using Capacity Factor)

$$a=k2/k1$$

wherein,
k1=Capacity Factor of Late Eluting Peak
k2=Capacity Factor of Early Eluting Peak The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A method of purifying 1,2,5,6-hexanetetrol (HTO) comprising: contacting a mixture comprising HTO and other $C_1$-$C_6$ alcohols and polyols with a resin material adapted for chromatography, under conditions where HTO preferentially associates with the resin material relative to other components in the mixture; and eluting HTO from said resin material with a solvent.

2. The method according to claim 1, wherein said mixture is a product of a sugar alcohol hydrogenation.

3. The method according to claim 2, wherein said sugar alcohol is selected from the group consisting of: sorbitol, mannitol, galactitol, fucitol, iditol, inositol, maltitol, and mixtures thereof.

4. The method according to claim 2, wherein said sugar alcohol is sorbitol.

5. The method according to claim 1, wherein said mixture comprises HTO, glycerol, volatile alcohols, sorbitol, water, and ionic species.

6. The method according to claim 1, wherein said resin material is either 1) a non-functionalized resin material, or 2) is either an acidic or basic functionalized resin in neutral form.

7. The method according to claim 1, wherein said resin material adapted for chromatography has a matrix composed of a polystyrene divinyl-benzene material.

8. The method according to claim 6, wherein said resin material has either 1) a Gaussian particle size distribution, or 2) a mono-dispersed particle size.

9. The method according to claim 1, wherein said resin material has a particle size in a range from about 200 μm to about 850 μm.

10. The method according to claim 9, wherein said resin material has a particle size in a range from about 250 μm to about 500 μm.

11. The method according to claim 1, wherein said resin material has an operational temperature in a range of about 15° C. to about 100° C.

12. The method according to claim 1, wherein an elution solvent is selected from the group consisting of deionized water, methanol, butanol, isopropanol, simple aliphatic alcohols, or a mixture thereof.

13. The method according to claim 1, wherein said method of purifying results in a yield of HTO of at least 60% wt./wt. at a purity level of at least 80%.

14. The method according to claim 13, wherein said yield is at least 75% wt./wt. at a purity level of at least 85%.

15. The method according to claim 1, wherein said mixture contacts an ion exchange resin before contacting said resin material adapted for chromatography.

16. The method according to claim 15, wherein said contacting with said ion exchange resin is performed either in a single step by contacting a mixed-bed acid/base resin, or in two steps by contacting an acid resin first, then base resin second or the reverse with base resin first and then acid resin second.

17. The method according to claim 15, wherein a fraction depleted of ions and containing HTO is obtained after contacting with the ion exchange resin and said fraction is concentrated by evaporation.

18. The method according to claim 17, wherein said evaporation method is selected from the group consisting of vacuum evaporation, thin film evaporation (TFE) and a combination of both vacuum and TFE.

19. The method according to claim 1, wherein resin material adapted for chromatography is loaded onto a simulated-moving bed (SMB) apparatus, and said SMB apparatus is operated to perform continuous chromatographic separation of HTO.

20. A method of purifying 1,2,5,6 hexanetetrol (HTO) from a reaction mixture comprised of HTO and other byproducts of a hydrogenation reaction of a sugar alcohol comprising:
   a) contacting said reaction mixture with a strong acid ion exchange resin to obtain a first eluent fraction depleted of cationic species;
   b) contacting said first eluent fraction with a strong basic ion exchange resin to obtain a second eluent fraction depleted of anionic species;

c) evaporating said second eluent fraction under vacuum and retaining a first bottoms fraction depleted of water, volatile alcohols and lower boiling diol;
d) subjecting said first bottoms fraction to a thin film evaporation and retaining a second bottoms fraction depleted of glycerol;
e) contacting said second bottoms fraction with a non-functionalized chromatography resin, wherein the resin is loaded into a simulated moving bed chromatography apparatus;
f) eluting said chromatography resin with deionized water; and
g) collecting a fraction enriched in HTO as compared to said hydrogenation reaction mixture.

* * * * *